United States Patent
Savall et al.

(10) Patent No.: US 11,653,988 B2
(45) Date of Patent: May 23, 2023

(54) MITIGATING ELECTROMAGNETIC FIELD DISTORTION FOR A SURGICAL ROBOTIC SYSTEM

(71) Applicant: Verb Surgical Inc., Mountain View, CA (US)

(72) Inventors: Joan Savall, Palo Alto, CA (US); Denise Ann Miller, Scotts Valley, CA (US); Hamid Reza Sani, Belmont, CA (US)

(73) Assignee: Verb Surgical Inc., Santa Clara, CA (US)

( * ) Notice: Subject to any disclaimer, the term of this patent is extended or adjusted under 35 U.S.C. 154(b) by 711 days.

(21) Appl. No.: 16/525,417

(22) Filed: Jul. 29, 2019

(65) Prior Publication Data

US 2021/0030495 A1 Feb. 4, 2021

(51) Int. Cl.
*A61B 34/35* (2016.01)
*A61B 34/20* (2016.01)
(Continued)

(52) U.S. Cl.
CPC .............. *A61B 34/35* (2016.02); *A61B 34/20* (2016.02); *A61B 34/74* (2016.02); *A61B 34/76* (2016.02);
(Continued)

(58) Field of Classification Search
CPC ......... A61B 34/35; A61B 34/20; A61B 34/74; A61B 34/76; A61B 2017/00199;
(Continued)

(56) References Cited

U.S. PATENT DOCUMENTS

| 8,190,238 | B2 * | 5/2012 | Moll ...................... A61B 34/71 715/702 |
| 9,733,336 | B2 * | 8/2017 | Shen ....................... G01S 5/021 |

(Continued)

FOREIGN PATENT DOCUMENTS

| WO | WO-0163312 A1 * | 8/2001 | ........... G01B 3/1084 |
| WO | 2014198796 | 12/2014 | |

OTHER PUBLICATIONS

International Search Report and Written Opinion for International Application No. PCT/US2019/044523 dated Apr. 28, 2020, 9 pages.

*Primary Examiner* — Julian W Woo
(74) *Attorney, Agent, or Firm* — Aikin & Gallant, LLP

(57) ABSTRACT

Surgical systems including a user console for controlling a surgical robotic tool are described. A witness sensor and a reference sensor can be mounted on the user console to measure an electromagnetic field distortion near a location, and to measure deformation of the location, respectively. Distortion in the electromagnetic field can be detected based on the measurements from the witness sensor and the reference sensor. An alert can be generated, or teleoperation of the surgical tool can be adjusted or paused, when a user interface device used to control the surgical tool is within a range of the distortion. The distortion can be from a known source, such as from actuation of a haptic motor of the user interface device, and the user console can adjust the actuation to reduce the likelihood that the distortion will disrupt surgical tool control. Other embodiments are described and claimed.

21 Claims, 7 Drawing Sheets

(51) Int. Cl.
    *A61B 34/00*     (2016.01)
    *A61B 34/30*     (2016.01)
    *A61B 17/00*     (2006.01)

(52) U.S. Cl.
    CPC ........... *A61B 2017/00199* (2013.01); *A61B 2017/00398* (2013.01); *A61B 2017/00973* (2013.01); *A61B 2034/2051* (2016.02); *A61B 2034/2055* (2016.02); *A61B 2034/302* (2016.02); *A61B 2034/742* (2016.02); *A61B 2034/743* (2016.02); *A61B 2034/744* (2016.02)

(58) Field of Classification Search
    CPC ...... A61B 2034/2051; A61B 2034/302; A61B 2017/00039; A61B 2034/2072
    See application file for complete search history.

(56) References Cited

U.S. PATENT DOCUMENTS

| | | | |
|---|---|---|---|
| 10,827,913 B2 * | 11/2020 | Ummalaneni | A61B 34/30 |
| 10,835,153 B2 * | 11/2020 | Rafii-Tari | A61B 34/25 |
| 11,490,782 B2 | 11/2022 | Rafii-Tari et al. | |
| 2005/0098745 A1 | 5/2005 | Peng | |
| 2014/0354300 A1 | 12/2014 | Ramachandran et al. | |
| 2018/0125604 A1 | 5/2018 | Hartmann et al. | |
| 2019/0000560 A1 | 1/2019 | Berman et al. | |
| 2020/0078113 A1 * | 3/2020 | Sawhney | A61B 34/35 |

\* cited by examiner

MITIGATING ELECTROMAGNETIC FIELD DISTORTION FOR A SURGICAL ROBOTIC SYSTEM

BACKGROUND

Field

Embodiments related to robotic systems are disclosed. More particularly, embodiments related to surgical robotic systems are disclosed.

Background Information

Endoscopic surgery involves looking into a patient's body and performing surgery inside the body using endoscopes and other surgical tools. For example, laparoscopic surgery can use a laparoscope to access and view an abdominal cavity. Endoscopic surgery can be performed using manual tools and/or a surgical robotic system having robotically-assisted tools.

A surgical robotic system may be remotely operated by a surgeon to control robotically-assisted tools and at least one camera located at an operating table. The surgeon may use a computer console located in the operating room, or it may be located in a different city, to command a robot to manipulate the surgical tool and camera. The robot uses the surgical tools to perform surgery, with the visualization aid provided by the camera.

Control of the surgical robotic system may require control inputs from the surgeon. For example, the surgeon may hold in her hand a user input device such as a joystick or a computer mouse that she manipulates to generate the signals for the control commands that control motion of the surgical robotic system components, e.g., the surgical tool or the camera.

SUMMARY

Surgical robotic systems including a user console for controlling a surgical robotic tool are described. The user console can communicate with a user interface device (UID) to detect a position, orientation, or both, of the UID within an electromagnetic (EM) tracking space. The detected position or orientation of the UID may be correlated to control of a surgical robotic tool, by for example mimicking the motion of the UID at the tool. Detection of the position or orientation, however, may be disrupted by distortion of an EM field within the EM tracking space. The surgical robotic system can include one or more response mechanisms to reduce the likelihood that such EM distortion will disrupt operation of the UID or control of the surgical robotic tool.

In an embodiment, a surgical robotic system includes a user console used to control a surgical robotic system in accordance with motion of a UID. More particularly, the user console provides control signals to control one or more actuators and/or surgical tools of the surgical robotic system in accordance with motion of the UID. The control signals represent spatial state signals that may be produced by an EM tracking subsystem, and in particular received from the UID, in response to movement of the UID within an EM field of an EM tracking space. To reduce the likelihood that the UID EM readings are disrupted by a distortion within the EM field, the user console can include a witness sensor mounted at a particular location, and a reference sensor. The reference sensor may be mounted adjacent to the witness sensor, or on the UID. The witness sensor can sense or measure a witness EM reading of the EM field. The witness EM reading can reflect a distortion of the EM field. The reference sensor can sense or measure a non-electromagnetic event, such as a deformation of the user console at the location of the witness sensor. The distortion that is reflected in the witness EM reading and the deformation that is reflected in the deformation reading may coincide in time, partially or wholly. The deformation reading can be used to validate the witness EM reading events. For example, when the witness EM reading and the deformation reading do not "match", e.g. coincide in time, it may be determined that the distortion reflected in the witness EM reading results from an actual EM distortion and not a mechanical vibration of the witness sensor. When the witness EM reading is validated, the user console can have several responses. For example, the user console can generate a notification of the detected distortion to cause an alert (e.g., visual, audible, or both, in terms of being perceived by a user of the surgical robotic system) indicating an existence of the distortion, a location of the distortion, or a cause of the distortion. The user console can also adjust or pause motion of an actuator and/or surgical tool of the surgical robotic system, e.g., immediately in response to the validation.

In an embodiment, the cause of distortion within the EM field is known (e.g., hypothesized). For example, the distortion may originate from actuation of a haptic motor incorporated in the UID. The user console may alter a manner in which actuation pulses are input to the haptic motor, or a manner in which UID EM readings are sampled from the UID, to reduce the likelihood that the actuation-caused distortion will affect the spatial state signal samples. For example, the user console may not actuate the haptic motor (e.g., prevents actuation of the haptic motor) while it is sampling spatial state signals (that are being used in real-time to control the motion of an actuator and/or a surgical tool of the surgical robotic system during a surgical operation). Alternatively, the user console may ignore spatial state signals (samples) received while the haptic motor is being actuated. The user console may interlace the spatial state and actuation pulse signals by for example controlling the timing of the actuation pulses, generating an actuation pulse for the haptic motor only during the time interval between samples of a spatial state signal. Accordingly, the user console can adjust the actuation to reduce the likelihood that the EM distortion will disrupt surgical tool control.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment of the invention in this disclosure are not necessarily to the same embodiment, and they mean at least one. Also, in the interest of conciseness and reducing the total number of figures, a given figure may be used to illustrate the features of more than one embodiment of the invention, and not all elements in the figure may be required for a given embodiment.

DETAILED DESCRIPTION

Figure 1:
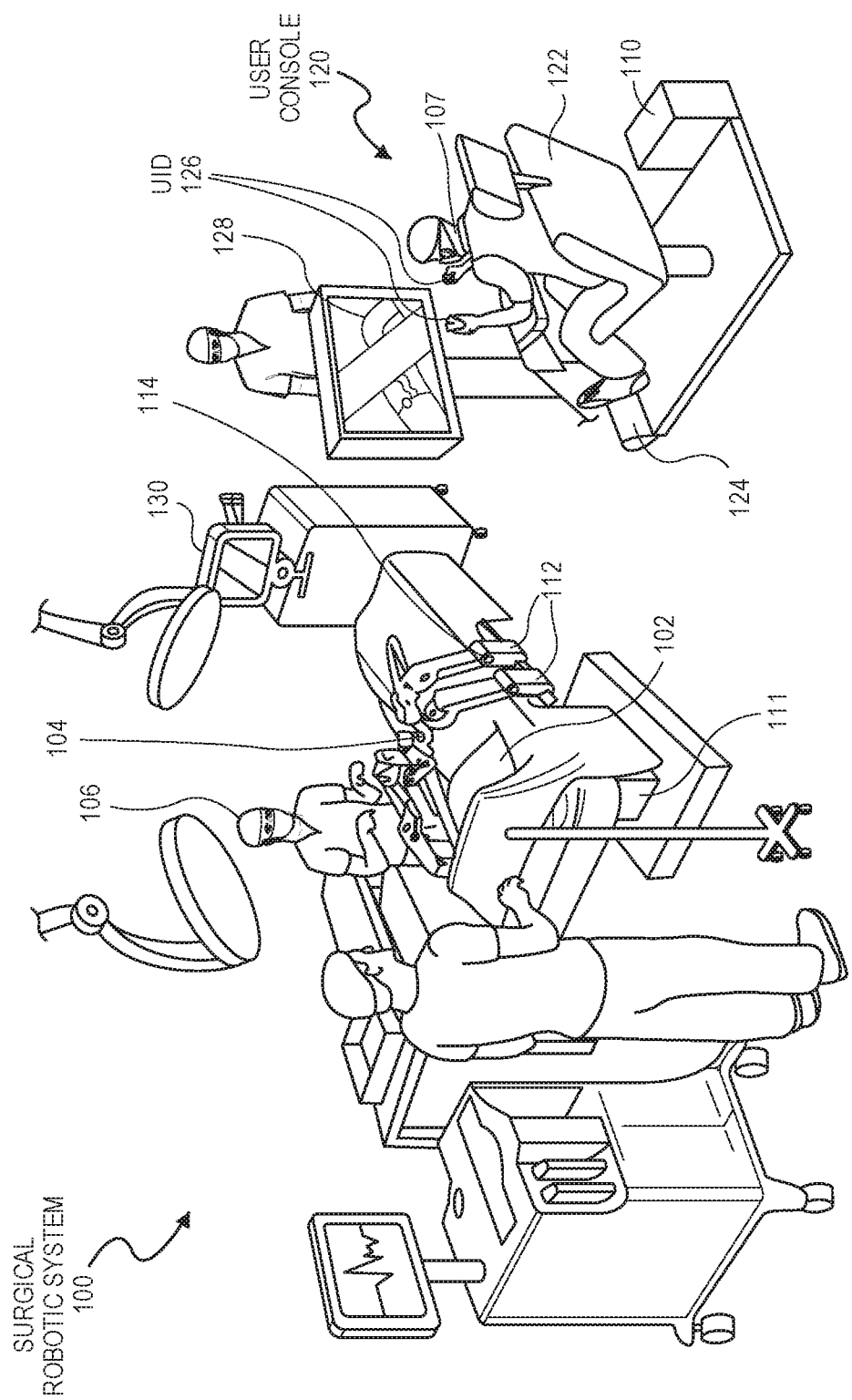
FIG. 1 is a pictorial view of a surgical robotic system in an operating arena, in accordance with an embodiment.

Embodiments describe a surgical robotic system having a user console for controlling a surgical robotic system. The user console may, however, be used to control other systems, such as interventional cardiology systems, vision systems, or aircraft systems, to name only a few possible applications.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "left" may indicate a first direction away from a reference point, e.g., to the left of a seat. Similarly, "right" may indicate a location in a second direction opposite to the first direction, e.g., to the right of the seat. Such terms are provided to establish relative frames of reference, however, and are not intended to limit the use or orientation of a surgical robotic system to a specific configuration described in the various embodiments below.

In an aspect, a surgical robotic system includes a user console for controlling a surgical robotic tool. The surgical robotic system has one or more electromagnetic (EM) field distortion responses to reduce the likelihood that distortions occurring in an EM field of the user console will affect control signals transmitted to the surgical robotic tool. In an embodiment, the user console includes reference sensors paired with respective witness sensors to determine whether a distortion reflected in a witness EM reading from a witness sensor is an actual EM distortion or an artifact of a mechanical movement of the witness sensor. When the witness EM reading from the witness sensor is validated by the reference sensor as reflecting a real distortion, the user console can initiate several responses, including: alerting an operator about the distortion, providing guidance to the operator about how to correct the distortion, or pausing teleoperation of the surgical robotic tool. The distortion can be from a known, e.g., hypothesized, source, such as from actuation of a haptic motor of a user interface device used to control the surgical robotic tool. Accordingly, the user console can take actions to mitigate the effect of the known distortions such as, but not limited to: not actuating the haptic motor when surgical operations are being performed, ignoring control signals from the user interface device when the haptic motor is actuated, supplementing controls signals from the user interface device with control signals from other sensors that are unaffected by the distortion, or interlacing the control signals received from the user interface device with the actuation signals sent to the user interface device. These response signals and others described below may be used by the user console to reduce the likelihood that EM distortion will disrupt surgical tool control.

Referring to FIG. 1, this is a pictorial view of an example robotic system in an operating arena. A surgical robotic system 100 includes a user console 120, a control tower 130, and one or more surgical robotic arms 112 at a surgical robotic platform 111, e.g., a table, a bed, etc. The system 100 can incorporate any number of devices, tools, or accessories used to perform surgery on a patient 102. For example, the system 100 may include one or more surgical tools 104 used to perform surgery. A surgical tool 104 may be an end effector that is attached to a distal end of a surgical arm 112, for executing a surgical procedure.

Each surgical tool 104 may be manipulated manually, robotically, or both, during the surgery. For example, surgical tool 104 may be a tool used to enter, view, or manipulate an internal anatomy of patient 102. In an embodiment, surgical tool 104 is a grasper that can grasp tissue of patient 102. Surgical tool 104 may be controlled manually, by a bedside operator 106; or it may be controlled robotically, via actuated movement of the surgical robotic arm 112 to which it is attached. Robotic arms 112 are shown as a table-mounted system, but in other configurations the arms 112 may be mounted in a cart, ceiling or sidewall, or in another suitable structural support.

Generally, a remote operator 107, such as a surgeon or other operator, may use the user console 120 to remotely manipulate the arms 112 and/or surgical tools 104, e.g., by teleoperation. The user console 120 may be located in the same operating room as the rest of the system 100, as shown in FIG. 1. In other environments, however, the user console 120 may be located in an adjacent or nearby room, or it may be at a remote location, e.g., in a different building, city, or country. The user console 120 may comprise a seat 122, foot-operated controls 124, one or more handheld user interface devices, UIDs 126, and at least one user display 128 that is configured to display, for example, a view of the surgical site inside patient 102. In the example user console 120, remote operator 107 is sitting in seat 122 and viewing the user display 128 while manipulating a foot-operated control 124 and a handheld UID 126 in order to remotely control the arms 112 and surgical tools 104 (that are mounted on the distal ends of the arms 112). Foot-operated control(s) 124 can be foot pedals, such as seven pedals, that generate motion control signals when actuated. User console 120 may include one or more additional interface devices (FIG. 11) such as a keyboard or joystick, to receive manual inputs to control operations of user console 120 or surgical robotic system 100.

In some variations, bedside operator 106 may also operate system 100 in an "over the bed" mode, in which bedside operator 106 (user) is now at a side of patient 102 and is simultaneously manipulating a robotically-driven tool (end effector attached to arm 112), e.g., with a handheld UID 126 held in one hand, and a manual laparoscopic tool. For example, the bedside operator's left hand may be manipulating the handheld UID 126 to control a robotic component, while the bedside operator's right hand may be manipulating a manual laparoscopic tool. Thus, in these variations, bedside operator 106 may perform both robotic-assisted minimally invasive surgery and manual laparoscopic surgery on patient 102.

During an example procedure (surgery), patient 102 is prepped and draped in a sterile fashion to achieve anesthesia. Initial access to the surgical site may be performed manually while the arms of the robotic system 100 are in a stowed configuration, e.g., under platform 111, or withdrawn configuration (to facilitate access to the surgical site). Once access is completed, initial positioning or preparation of the robotic system including its arms 112 may be performed. Next the surgery proceeds with the remote operator 107 at the user console 120 utilizing the foot-operated controls 124 and the UIDs 126 to manipulate the various end effectors and perhaps an imaging system, to perform the surgery. Manual assistance may also be provided at the procedure bed or table, by sterile-gowned bedside personnel, e.g., bedside operator 106, who may perform tasks such as retracting tissues, performing manual repositioning, and tool exchange upon one or more of the robotic arms 112. Non-sterile personnel may also be present to assist remote operator 107 at the user console 120. When the procedure or surgery is completed, the system 100 and/or user console 120 may be configured or set in a state to facilitate post-operative procedures such as cleaning or sterilization, and healthcare record entry or printout via user console 120.

In one embodiment, remote operator 107 holds and moves UID 126 to provide an input command to move a robot arm actuator 114 in robotic system 100. UID 126 may be communicatively coupled to the rest of robotic system 100, e.g., via a console computer system 110. UID 126 can generate spatial state signals corresponding to movement of UID 126, e.g., position and orientation of the handheld housing of the UID, and the spatial state signals may be input signals to control a motion of the robot arm actuator 114. Robotic system 100 may use control signals derived from the spatial state signals to control proportional motion of actuator 114. In one embodiment, a console processor of console computer system 110 receives the spatial state signals, also referred to herein as UID EM readings, from UID 126 and uses the UID EM readings to generate the corresponding control signals. Based on these control signals, which control how the actuator 114 is energized to move a segment or link of arm 112, the movement of corresponding surgical tool 104 that is attached to the arm may mimic the movement of UID 126. For example, console processor can pause motion of a corresponding actuator when UID 126 is within a range of a detected distortion in an EM field, as described below. Similarly, interaction between remote operator 107 and UID 126 can generate for example a grip control signal that causes a jaw of a grasper of surgical tool 104 to close and grip the tissue of patient 102.

Surgical robotic system 100 may include several UIDs 126, where respective control signals are generated for each UID that control the actuators and the surgical tool (end effector) of a respective arm 112. For example, remote operator 107 may move a first UID 126 to control the motion of actuator 114 that is in a left robotic arm, where the actuator responds by moving linkages, gears, etc., in that arm 112. Similarly, movement of a second UID 126 by remote operator 107 controls the motion of another actuator 114, which in turn moves other linkages, gears, etc., of the robotic system 100. Robotic system 100 may include a right arm 112 that is secured to the bed or table to the right side of the patient, and a left arm 112 that is at the left side of the patient. An actuator 114 may include one or more motors that are controlled so that they drive the rotation or linear movement of a joint of arm 112 to, for example, change relative to the patient an orientation of an endoscope or a grasper of the surgical tool that is attached to that arm. Motion of several actuators 114 in the same arm 112 can be controlled by the spatial state signals generated from a particular UID 126. UIDs 126 can also control motion of respective surgical tool graspers. For example, each UID 126 can generate a respective grip signal to control motion of an actuator, e.g., a linear actuator, that opens or closes jaws of the grasper at a distal end of the surgical tool to grip tissue within patient 102.

In some aspects, the communication between platform 111 and user console 120 may be through a control tower 130, which may translate user commands that are received from user console 120 (and more particularly from console computer system 110) into robotic control commands that are transmitted to arms 112 on robotic platform 111. The control tower 130 may also transmit status and feedback from platform 111 back to user console 120. The communication connections between the robotic platform 111, user console 120, and control tower 130 may be via wired and/or wireless links, using any suitable ones of a variety of data communication protocols. Any wired connections may be optionally built into the floor and/or walls or ceiling of the operating room. Robotic system 100 may provide video output to one or more displays, including displays within the operating room as well as remote displays that are accessible via the Internet or other networks. The video output or feed may also be encrypted to ensure privacy and all or portions of the video output may be saved to a server or electronic healthcare record system.

Figure 2:
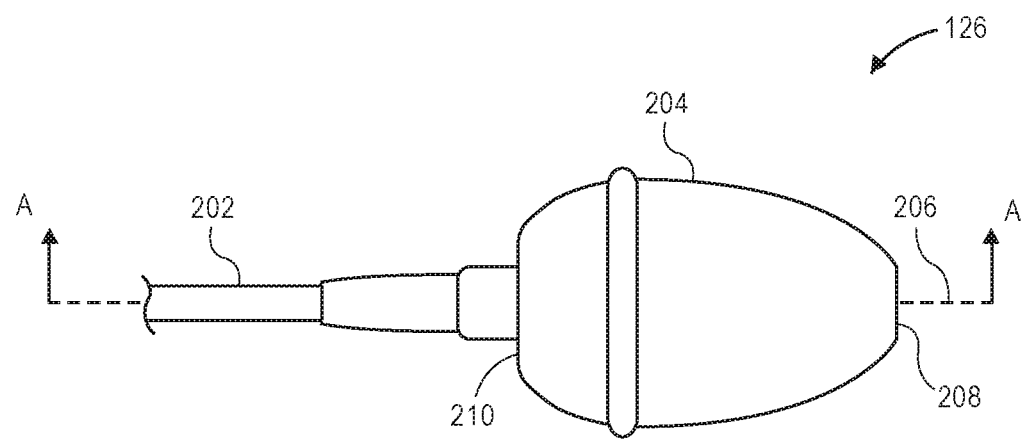
FIG. 2 is a side view of a user interface device, in accordance with an embodiment.

Referring to FIG. 2, a side view of a user interface device is shown in accordance with an embodiment. Remote operator 107 may hold and move an ungrounded user interface device (UID) 126 to provide an input command to the console computer system 110. In an embodiment, UID 126 includes a device body 204 extending in a longitudinal direction along a central axis 206. For example, device body 204 may extend longitudinally from a proximal end 208 that is normally cupped within a hand of remote operator 107 during use. Device body 204 may extend to a distal end 210 having a forward-facing surface. UID 126 can be considered to be ungrounded because it is capable of being held and moved freely in space by a user. More particularly, UID 126 may not be connected to an external frame, link, or support, but rather motion of UID 126 may be constrained only by a range of motion of the user's arms.

UID 126 may be communicatively coupled to actuator 114, e.g., via console computer system 110. For example, UID 126 can generate spatial state signals corresponding to movement of the UID 126, and the spatial state signals can be transmitted to console computer system 110 through an electrical cable 202. The spatial state signals from the UID 126 can be used to control various elements of surgical robotic system 100, depending on a mode of operation. More particularly, UID 126 may be used in a surgery mode or a non-surgery mode to control different system functions.

When UID 126 is used in the surgery mode, spatial state signals from UID 126 can control proportional motion of a corresponding actuator 114. Actuator 114 may be coupled to a corresponding surgical tool 104, e.g., via arm 112, and thus, the corresponding surgical tool 104 may be moved by the corresponding actuator 114 based on the spatial state signals. Similarly, interaction between remote operator 107 and UID 126 can generate a grip signal to cause a jaw of a grasper of surgical tool 104 to close and grip the tissue of patient 102. For example, when user squeezes UID 126 between two or more fingers, the jaw may mimic the motion of the fingers and squeeze the tissue.

When UID 126 is used in a non-surgery mode, UID 126 can control elements of user console 120. For example, spatial state signals from UID 126 can control a graphical user interface displayed on console computer system 110. More particularly, spatial state signals can control a cursor element on display 128 of console computer system 110. Movement of UID 126 in the non-surgery mode may be characterized as coarse movement and movement of UID 126 in the surgery mode may be characterized as fine movement because a speed or magnitude of UID movement in the non-surgery mode may be greater than a speed or magnitude of UID movement in the surgery mode.

The surgical robotic system may include several UIDs 126. Each UID 126 can generate a respective control signal. For example, remote operator 107 may move a first UID 126 to control a function of a first actuator 114 or a first GUI element of console computer system 110. Similarly, movement of a second UID 126 (not shown) can control function of a second actuator 114 or another GUI element of console computer system 110. Accordingly, the surgical robotic system can include one or more UIDs 126 having the structure described below.

Figure 3:
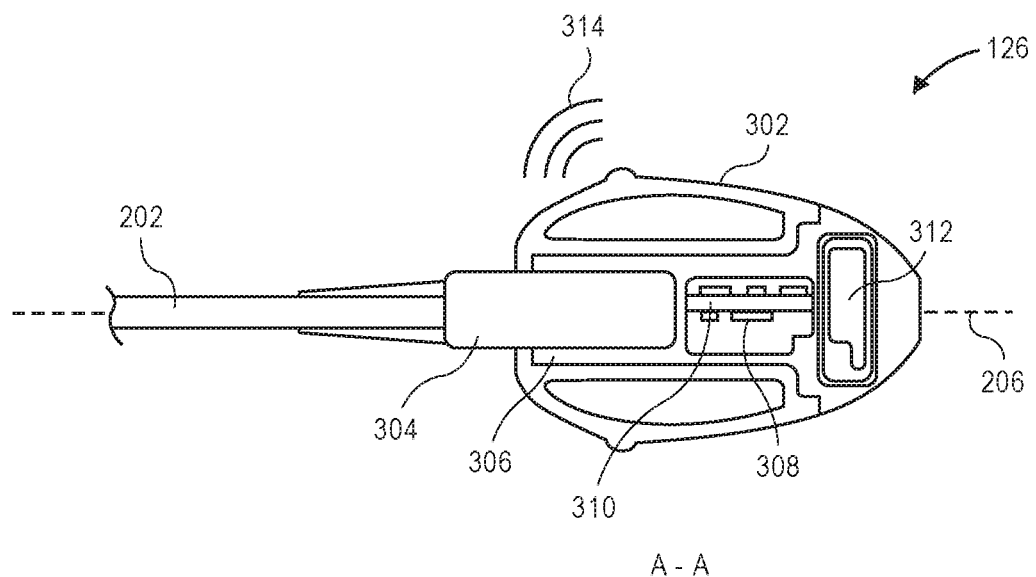
FIG. 3 is a sectional view of a user interface device, taken about line A-A of FIG. 2, in accordance with an embodiment.

Referring to FIG. 3, a sectional view of a user interface device, taken about line A-A of FIG. 2, is shown in accordance with an embodiment. Device body 204 can have an outer surface 302 extending around central axis 206. Outer surface 302 of device body 204 may surround a cavity. The cavity within device body 204 can receive a tracking sensor 304 used to track movement of UID 126. More particularly, tracking sensor 304 may be mounted within device body 204. Tracking sensor 304 can be fixed to a device member 306. Device member 306 can be attached to device body 204. Thus, tracking sensor 304 may experience the same movement as device body 204.

Tracking sensor 304 can be an EM sensor configured to generate spatial state signals that are UID EM readings of the EM field. For example, the UID EM sensor can generate a spatial state signal in response to movement of device body 204. Tracking sensor 304 can detect a position and/or orientation of device body 204 when user moves UID 126. For example, tracking sensor 304 may detect translation, rotation, or tilting of device body 204 within a workspace. In an embodiment, tracking sensor 304 generates the spatial state signal in response to movement of UID 126 within the EM field of the workspace.

UID 126 can include other sensors to detect movement of device body 204. For example, UID 126 can include an inertial measurement unit (IMU) 308. IMU 308 can be mounted on a printed circuit board 310 in or on device body 204 of UID 126. IMU 308 may include an accelerometer and/or a gyroscope or other inertial sensors. IMU 308 may generate a second spatial state signal in response to movement of UID 126. That is, IMU 308 may generate the second spatial state signal that corresponds to the same movement of UID 126 tracked by tracking sensor 304. Accordingly, UID 126 may simultaneously generate the spatial state signal from tracking sensor 304 and the second spatial state signal from IMU 308 to control function(s) of the robotic system.

In an embodiment, UID 126 can include a haptic motor 312 capable of generating a haptic cue 314 when actuated. Haptic cue 314 can be a mechanical vibration to indicate to remote operator 107 that a haptic trigger event has occurred. Haptic cue 314 can be generated in response to energizing haptic motor 312, which may include an electromechanical transducer such as a rotary motor, a linear motion motor, or other suitable vibrational or other tactile feedback motor. Haptic motor 312 may be controlled to provide haptic feedback to remote operator 107 in the form of tactile feedback. For example, a controller may actuate haptic motor 312 to drive a rotating eccentric mass and generate a vibration that communicates the occurrence of the haptic trigger event. Haptic cues 314 may be generated using other known haptic technologies. Different patterns, e.g., duty cycle, pattern of an irregular on-off cycle, speed, etc., may indicate different haptic trigger events to remote operator 107. For example, a haptic trigger event may be when remote operator 107 has moved UID 126 in a direction to a predetermined limit of the workspace, e.g., to a boundary of the workspace. Haptic cue 314 may be emitted to alert remote operator 107 that UID 126 must be repositioned within the workspace to continue movement in the direction. Other examples of events triggering haptic feedback to remote operator 107 include actuation of an end effector, e.g., firing of a cauterization tool, loss of communication with UID 126, e.g., due to power loss, misalignment of UID 126 relative to a calibrated or known reference frame, or detection of potential collision between components of the robotic system, e.g., between arms 112.

UID 126 may include a feedback mechanism capable of generating other feedback cues. For example, UID 126 may include an electroacoustic transducer to generate an audio cue such as a tone, warning, etc. UID 126 may include an electro-optical transducer, e.g., a light emitting diode or a display, to generate a visual cue such as an error code or other visual information. The visual or audio cues can be considered to be a type of haptic cue 314, and accordingly, the electroacoustic transducer and electro-optical transducer can be considered to be a type of haptic motor 312.

Figure 4:
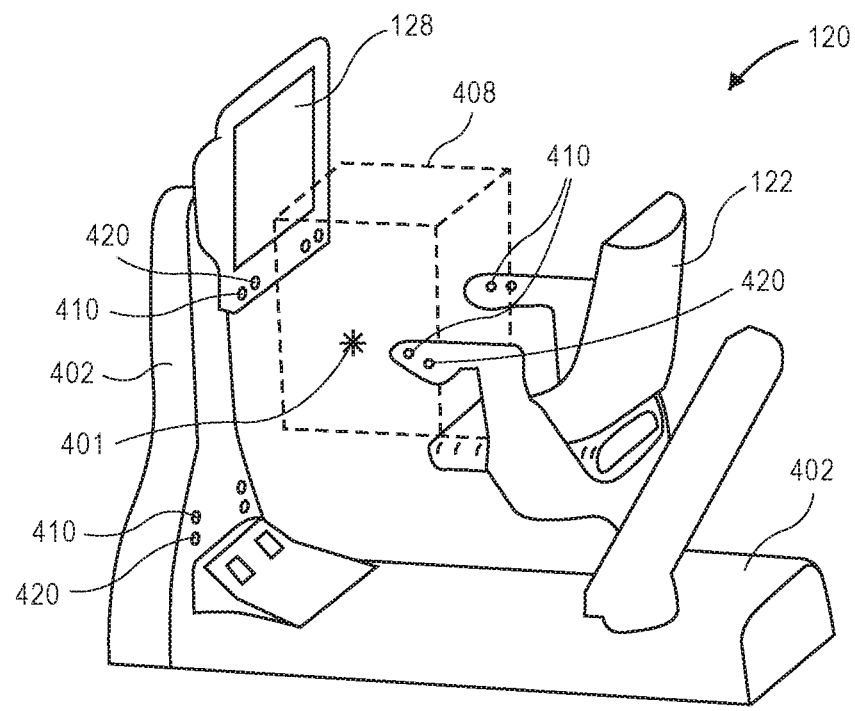
FIG. 4 is a perspective view of a user console, in accordance with an embodiment.

Referring to FIG. 4, a perspective view of a user console is shown in accordance with an embodiment. User console 120 can include a base 402 to support seat 122 and display 128 of the surgical robotic system. Remote operator 107 may sit on seat 122 while viewing display 128 during a surgical procedure. User console 120 can include a tracking subsystem to monitor movement of UID 126. For example, the tracking subsystem can be an optical tracking subsystem including components to monitor movement of UID 126 based on detection of a marker on UID 126. The marker may be identifiable in an image to determine a position or orientation of UID 126. The tracking subsystem may be an EM tracking subsystem having an EM source. The EM source can generate an EM tracking space 408, and remote operator 107 can hold UID 126 within EM tracking space 408 to cause movement of surgical tool 104 during the surgical procedure. More particularly, EM tracking space 408 may be the workspace within which remote operator 107 may move UID 126 to generate the spatial state signal.

User console 120 may include a source of an EM field (not shown). The source can be an EM generator mounted on user console 120. The EM generator may include a field generator to generate a position varying magnetic field that is used to establish a coordinate space. Accordingly, the EM generator can generate the EM field of the workspace within which UID 126 is manipulated. The EM field can be EM tracking space 408.

Tracking sensor 304 can be a magnetic tracking probe capable of measuring six degrees of freedom within EM tracking space 408. Tracking sensor 304 can be a sensor containing coils in which current is induced via the EM field. Tracking sensor 304 can have a known response to the EM field, and the response may be measured. By measuring the coil behavior, a position and orientation of tracking sensor 304, and thus UID 126, can be determined. The measured response may be output as the spatial state signal (UID EM readings) representing movement of UID 126 within EM tracking space 408.

Distortion of the EM field can cause inaccuracies in the spatial state signal generated by UID 126. For example, metals entering or passing near EM tracking space 408 can cause a distortion 401 in the EM field. When the EM field is distorted, the spatial state signal may be inaccurate and may not accurately control movement of surgical tool 104. For example, when distortion 401 is collocated with UID 126 in the EM field, the spatial state signal may erroneously represent a movement of UID 126 and cause actuator 114 to move surgical tool 104 even when remote operator 107 has held UID 126 stationary.

The surgical robotic system can include one or more witness sensors 410 mounted on user console 120 at respective locations. The witness sensors 410 can be EM sensors, and can communicate respective witness EM readings to the console processor of user console 120. As described below, the witness EM readings can reflect a distortion in the EM field, and thus, the console processor can process the witness EM readings to detect a distortion event within the EM field of EM tracking space 408.

Each witness sensor 410 may be configured to generate a witness EM reading of an EM field within EM tracking space 408. Witness sensor 410 can be an EM sensor in order to monitor the quality of the EM field. More particularly, the witness sensor(s) 410 can measure the EM field at known locations within or near EM tracking space 408. The witness EM reading can be a sensor signal containing real-time variation of a sensed environmental quantity, e.g., the quality of the EM field. The sensed data stream can reflect events or occurrences within the EM field. For example, the witness EM readings can reflect distortion 401 of the EM field. Since the tracking sensor 304 relies on the quality and stability of the EM field, when the witness EM reading from witness sensor(s) 410 reflect the distortion event, the spatial state signal from tracking sensor 304 can be handled differently by the console processor so as to prevent inaccurate movement of surgical tool 104.

Figure 5:
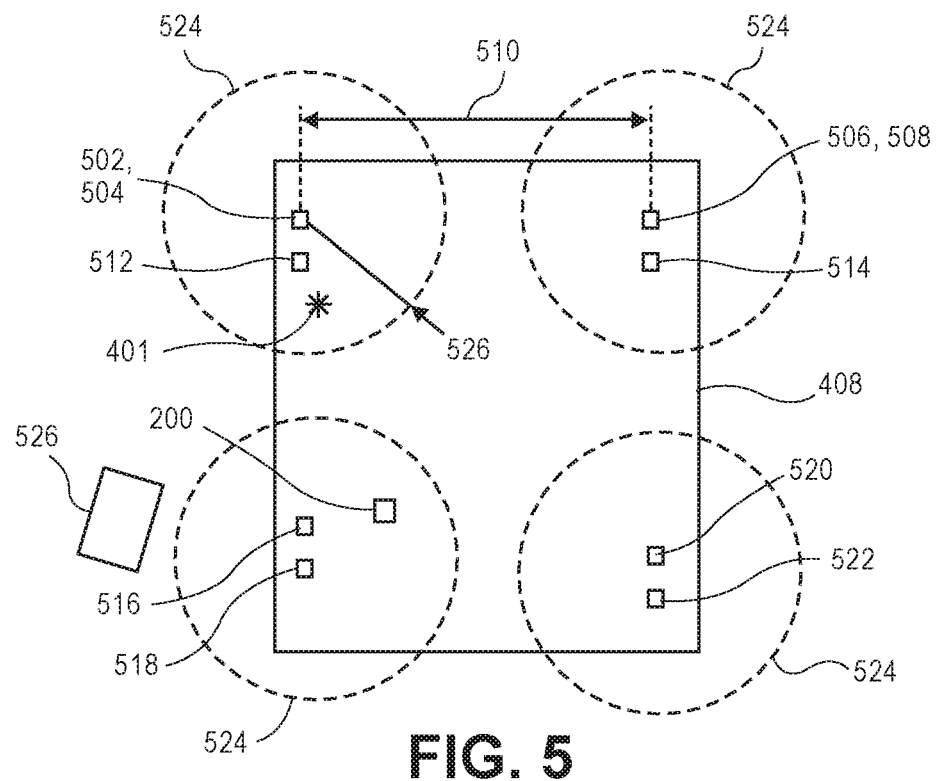
FIG. 5 is a pictorial view of an electromagnetic tracking space, in accordance with an embodiment.

Referring to FIG. 5, a pictorial view of an EM tracking space is shown in accordance with an embodiment. Witness sensors 410 may be vulnerable to false triggers. User console 120 can include a first witness sensor 502 mounted on user console 120 at a first location 504, and a second witness sensor 506 mounted on user console 120 at a second location 508. By way of example, first location 504 may be on a left armrest of seat 122, and second location 508 may be on a right armrest of seat 122. Second witness sensor 506 can generate a second witness EM reading of the EM field. The second witness EM reading can reflect a quality of the EM field around second witness sensor 506. First witness sensor 502 and second witness sensor 506 are assumed to be static, and thus, a distance 510 between witness sensors 502, 506 is known and expected to be constant (as determined by the console processor, which is communicatively coupled to both witness sensors 502) when there is no distortion of the EM field. When the witness EM readings from witness sensor 502 and second witness sensor 506 reflect a change in distance 510 between the witness sensors, the console processor can determine that a distortion occurred in the EM field. Accordingly, detecting distortion 401 of the EM field by the console processor may include detecting the distance change between first location 504 and second location 508. The detected distance change, however, may actually result from a mechanical movement of witness sensors 502, 506 relative to each other, rather than being caused by an EM field distortion. For example, the armrests can move if remote operator 107 shifts in seat 122. The movement of the armrests may be inaccurately detected as the distortion 401.

Mechanical vibrations of witness sensors 410 may be one source of unreliable witness EM readings. Aberrant witness EM readings can also be caused by localized temperature changes at the location where witness sensor 410 is mounted. More particularly, heating or cooling of first witness sensor 502 can trigger false reflections of a distortion in the witness EM reading when there is no actual distortion of the EM field.

To avoid false detections of EM field distortion, the surgical robotic system may include a reference sensor 420 mounted on user console 120 adjacent to each witness sensor 410. Each reference sensor 420 may generate a deformation reading in response to a non-EM event occurring at the location where the adjacent witness sensor 410 is mounted. Accordingly, as used herein, the term "adjacent" can refer to any distance at which reference sensor 420 can detect the non-EM event occurring at the mounting location of witness sensor 410. For example, a first reference sensor 512 may be mounted on the left armrest adjacent to first witness sensor 502, and a second reference sensor 514 may be mounted on the right armrest adjacent to second witness sensor 506. A first reference sensor 512 can be mounted on the left armrest to detect a deformation or movement of user console 120 at the location where the adjacent first witness sensor 502 is mounted, e.g., when remote operator 107 shifts in seat 122. Alternatively, first reference sensor 502 may be mounted on seat 122 below the left armrest and detect a temperature change at the location where the adjacent first witness sensor 502 is mounted. Accordingly, data from first witness sensor 502 and first reference sensor 512 may be fused to determine whether a distortion reflected in a witness EM reading from the witness sensor is real, or whether the reflected distortion results from the non-EM event, e.g., a mechanical deformation or a temperature change of user console 120. The deformation reading from first reference sensor 512 can therefore validate the witness EM reading from first witness sensor 502.

Reference sensors 420 may include a non-EM sensor for detecting mechanical movement. For example, first reference sensor 512 may include an IMU to generate a time-varying signal containing data reflecting mechanical deformation of the mounting location. More particularly, detecting the deformation may include measuring a movement of the IMU adjacent to the mounting location. Reference sensors 420 may include a non-EM sensor for detecting temperature. For example, first reference sensor 512 may include a temperature sensor to measure a temperature change at first location 504 when the heating or cooling is applied. More particularly, detecting the temperature change can include measuring a temperature change adjacent to the mounting location. Reference sensor 420 may include other non-EM sensors for measuring non-EM events within or near the EM field. Data from the non-EM sensors can be used to validate data from EM witness sensors 410.

In an embodiment, one or more references sensors 420 are mounted on UID 126. For example, reference sensor 420 can be contained within device body 204 as one of the other sensors described above. IMU 308 may be reference sensor 420, and may be mounted on and/or inside of UID 126 adjacent to tracking sensor 304 such that movement of device body 302 in free space causes corresponding movements of the UID EM sensor 304 and reference sensor 420.

User console 120 may include witness sensors 410 and reference sensors 420 around a boundary of EM tracking space 408. For example, a third witness sensor 516 and a third reference sensor 518 may be collocated on base 402 near a left foot rest. Similarly, a fourth witness sensor 520 and a fourth reference sensor 522 may be co-located on base 402 near a right foot rest. Each pair of sensors may monitor a respective region of EM tracking space 408. More particularly, when the fused data from witness sensor 410 and reference sensor 420 of a pair indicates that a true distortion of the EM field has occurred, the distortion may be within a range 524 of the location where the witness sensor 410 is mounted. Range 524 of each pair of sensors, may be predetermined. For example, sensor pairs located at the corners of a lower plane of a cube-shaped volume of interest may have a spherical range 524 with a predetermined radius 526. As described below, console computer system 110 may identify a location of the distortion relative to user console 120, and appropriately handle spatial state signals received from UID 126 within a range of the location. For example, when a metal object passes near first witness sensor 502, distortion 401 may occur within range 524 of first witness sensor 502, and spatial state signals generated by UID 126 located within the range 524 may be ignored until the distortion is eliminated.

Figure 6A:
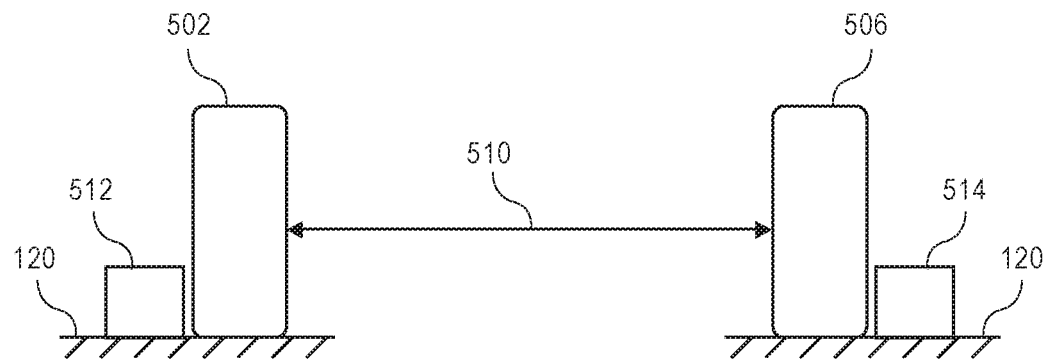
FIGS. 6A-6C are pictorial views of a witness sensor and a reference sensor mounted on a user console, in accordance with an embodiment.
Figure 6B:
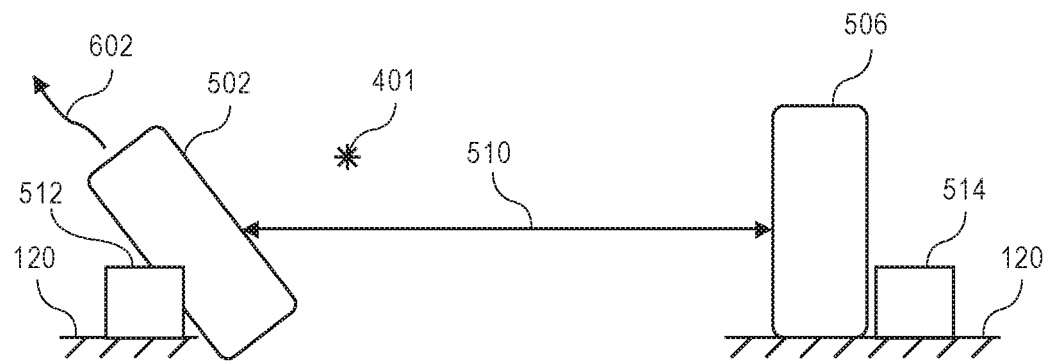
Figure 6C:
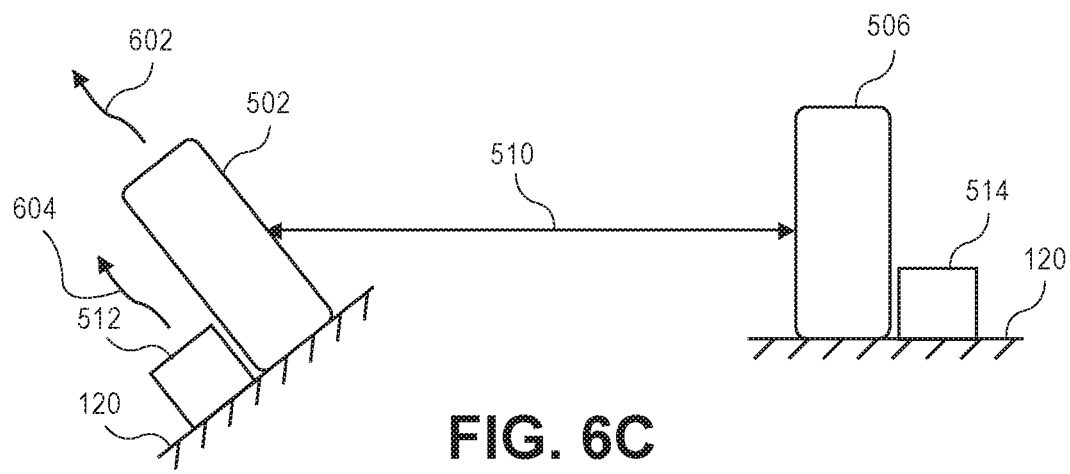

Referring to FIGS. 6A-6C, a pictorial view of a witness sensor 410 and a reference sensor 420 mounted on a user console 120 is shown in accordance with an embodiment. The illustrated examples are described using first witness sensor 502, first reference sensor 512, second witness sensor 506, and second reference sensor 514, mounted on user console 120 at distance 510 from each other. It will be appreciated, however, that the description applies similarly to any grouping of sensor pairs. Furthermore, although reference sensors in each of FIGS. 6A-6C detect motion, e.g., the reference sensors are IMUs, the description applies similarly to reference sensors that measure other non-EM events, e.g., temperature changes.

In FIG. 6A, a static scenario is illustrated in which distance 510 between first witness sensor 502 and second witness sensor 506, as reflected in the witness EM readings from the witness sensors, is constant. Similarly, neither of the deformation readings from first reference sensor 512 nor second reference sensor 514 reflect motion. That is, first location 504 on user console 120 and second location 508 on user console 120 are stable and fixed relative to each other. In the static scenario, the witness sensors 410 may not generate a witness EM reading 602 indicating a distortion of the EM field. Similarly, motion data from the reference sensors may indicate that there is no motion between first location 504 and second location 508, or that any motion between the locations is less than a predetermined deformation threshold.

In FIG. 6B, a static scenario is illustrated in which a distortion 401 occurs within the EM field. When distortion 401 occurs, e.g., when a metallic object passes near first witness sensor 502, a relative distance 510 between first witness sensor 502 and second witness sensor 506 as detected by user console 120 may change. First witness sensor 502 may generate a witness EM reading 602 indicating an existence of distortion 401. By contrast, user console 120 may be stable and first reference sensor 512 may remain stationary when the distortion occurs. Accordingly, relative readings of first witness sensor 502 and first reference sensor 512 may differ. Sensor readings that do not "match," e.g., contain data representing a distance change and a deformation that coincide in time, can indicate that the witness EM reading 602 indicating the distortion is accurate.

In FIG. 6C, a dynamic scenario is illustrated in which no distortion occurs within the EM field. The scenario may be dynamic because the location where first witness sensor 502 and second witness sensor 506 are mounted may move. For example, remote operator 107 may shift in seat 122 and cause the armrest to jostle. When the armrest moves, a relative distance 510 between first witness sensor 502 and second witness sensor 506 as detected by user console 120 may change. First witness sensor 502 may generate witness EM reading 602 indicating the existence of a distortion (that does not actually exist). Similarly, the deformation readings from first reference sensor 512 may reflect movement of armrest (or a change in another non-EM property at the location) and generate a deformation reading 604 representing the movement. Accordingly, relative readings of first witness sensor 502 and first reference sensor 512 may be the same. Sensor readings that "match," e.g., contain data representing a distance change and a deformation that coincide in time, can indicate that the distortion is falsely represented by first witness sensor 502, and witness EM reading 602 actually representing a system vibration, a mechanical movement, or another non-EM effect at the mounting location of first witness sensor 502.

Based on witness EM reading 602 and deformation reading 604, user console 120 can notify remote operator 107 of a potential distortion in the EM field. Furthermore, user console 120 can determine a likely location of the distortion, and notify remote operator 107 of the location. Additionally, given that a position of UID 126 relative to witness sensors 410 is known by the EM tracking system, user console 120 can determine when the detected distortion will affect the system. More particularly, user console 120 can notify remote operator 107 when UID 126 is near a witness sensor 410 measuring the distortion and/or pause teleoperation of surgical tool 104 by UID 126 when UID 126 comes within a predetermined proximity of the detected distortion. Accordingly, as described further below, user console 120 can provide a warning to remote operator 107 before the distortion affects performance of the system, and in some cases, may provide guidance to remote operator 107 to remove a cause of the distortion.

Figure 7:
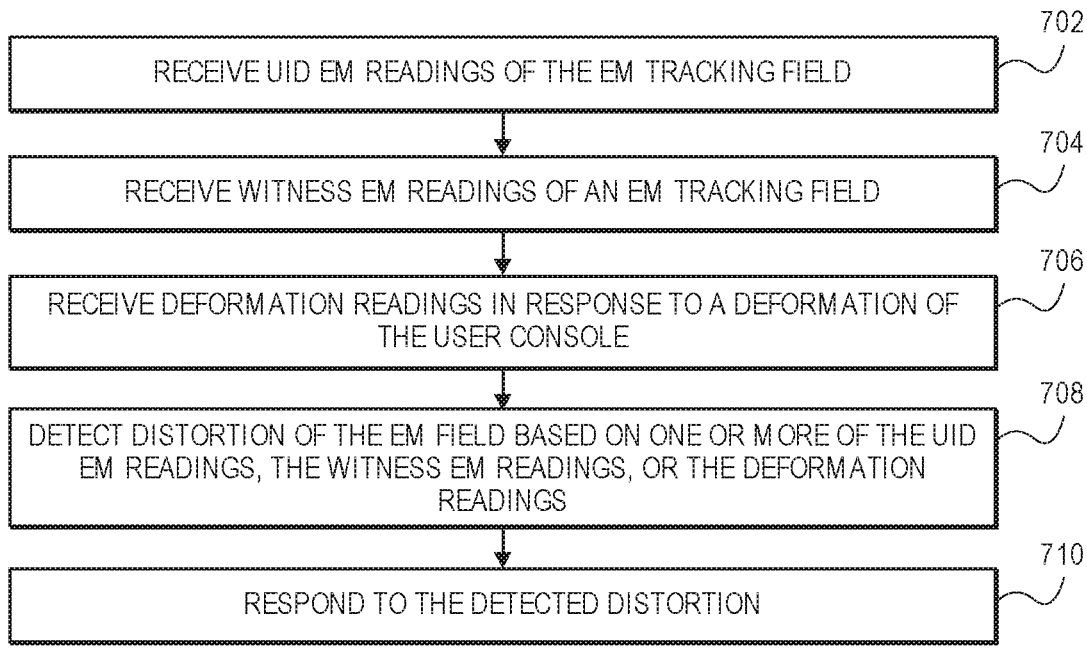
FIG. 7 is a flowchart of a method of detecting and responding to distortions in an electromagnetic tracking field in a surgical robotic system, in accordance with an embodiment.

Referring to FIG. 7, a flowchart of a method of detecting and responding to a distortion in an EM tracking field in a surgical robotic system is shown in accordance with an embodiment. The surgical robotic system can include a processor in communication with witness sensor 410 and reference sensor 420 of user console 120. For example, the processor may be a console processor (FIG. 11) contained in console computer system 110. The processor may be configured to respond, e.g., generate a distortion response signal, in response to a detected distortion. The processor can detect the distortion based on witness EM reading 602 and deformation reading 604. The response may include notifying remote operator 107 or otherwise altering control of the surgical robotic system when the distortion occurs within the EM field. The processor can execute instructions contained in a non-transitory computer-readable medium to cause the surgical robotic system to perform the method described below.

At operation 702, the processor receives UID EM readings of the EM tracking field. UID 126 generates the spatial state signals that are received by the processor. The spatial state signals provide the UID EM readings of the EM field. Accordingly, the console processor of user console 120, which is communicatively coupled to UID 126, can track one or more of position, orientation, or movement of UID 126 based on the UID EM readings.

At operation 704, the processor receives witness EM reading 602 of the EM tracking field from witness sensor 410. A stationary witness sensor 410, e.g., mounted on user console 120, generates witness EM reading 602 of the EM field. Witness EM reading 602 can reflect a distortion of the EM field. Accordingly, the console processor of user console 120, which is communicatively coupled to witness sensor 410, can detect distortion 401 within EM tracking space 408 of user console 120 based on witness EM reading 602.

At operation 706, the processor receives deformation readings 604 from reference sensor 420, e.g., mounted adjacent to witness sensor 410 on user console 120. Reference sensor 420 generates deformation readings 604 in response to a non-EM property or event at the mounting location. For example, deformation readings 604 may reflect a deformation of user console 120 at the location. Accordingly, the console processor of user console 120, which is communicatively coupled to reference sensor 420, can detect the deformation of user console 120.

At operation 708, the processor detects the distortion of the EM field based on one or more of the UID EM readings, the witness EM readings 602, or the deformation readings 604.

In an embodiment, the processor is communicatively coupled to witness sensor 410 and reference sensor 420, and the processor is configured to detect the distortion of the EM field based on both the witness EM readings 602 and the deformation readings 604. For example, the processor can generate the distortion response signal when, as shown in FIG. 6B, witness EM reading 602 and deformation reading 604 do not match. The processor may be configured to generate the distortion response signal when witness EM reading 602 from witness sensor 410 reflecting the presence of a distortion and deformation reading 604 indicates that there is disproportionately less deformation at the mounting location than witness EM reading 602 would otherwise indicate. More particularly, deformation reading 604 may indicate some movement at the location, such as movement corresponding to ambient noise or vibration. The deformation, however, may be less than a predetermined deformation threshold. Thus, deformation reading 604 may indicate movement by reference sensor 420 that is less than the detected relative movement between first witness sensor 502 and second witness sensor 506 resulting from the distortion. Deformation reading 604 can validate witness EM reading 602 to trigger the distortion response signal. More particularly, the processor can detect the distortion when witness EM readings 602 reflect the distortion in the EM field and deformation readings 604 reflect that the deformation is less than the predetermined deformation threshold.

At operation 710, the processor responds to the detected distortion. For example, the processor can generate a distortion response signal based on the received witness EM reading 602 and deformation reading 604.

Generation of the distortion response signal in response to the detected distortion can include adjusting one or more of a tracked position, orientation, or movement of UID 126 based on the detected distortion. For example, as described above, UID EM sensors 304 can generate UID EM readings that are used by the console processor to track one or more a position, an orientation, or a movement of UID 126. The console processor can be configured to adjust the tracking data reflecting the position, orientation, or movement of UID 126 based on witness EM readings 602 that measure or describe the distortion. Several examples of such adjustments are described immediately.

Adjustment of the one or more tracked position, orientation, or movement of UID 126 can be based on whether the detected distortion is below a distortion threshold. When the detected distortion is less than a certain amount of distortion, it may be assumed that the distortion will not have a significantly negative effect on the operation being performed. For example, a minor distortion may cause a cursor to skip slightly when the current operation is controlling a cursor on a display. Such skipping may be inconsequential to the procedure, and thus, not adjusting the one or more tracked position, orientation, or movement of UID 126 based on the detected distortion can conserve computing resources without negatively impacting the surgical procedure. Accordingly, the distortion may be ignored when the distortion value is below a distortion threshold.

Adjustment of the one or more tracked position, orientation, or movement of UID 126 can be based on whether UID 126 is within a range of the detected distortion. The processor can determine the location based on the predetermined range 524 of witness sensor 410. For example, when distortion 401 is detected based on a witness EM reading from first witness sensor 502, the processor can determine that the distortion 401 is within the predetermined range 524. The processor can also determine a location of UID 126 based on the UID EM readings, and thus, the processor can determine whether UID 126 is within the range of the detected distortion. In an embodiment, when UID 126 is within the range of the detected distortion and the deformation is less than the predetermined deformation threshold, the processor can adjust the one or more tracked position, orientation, or movement of UID 126.

In an embodiment, adjusting the one or more tracked position, orientation, or movement of UID 126 includes skipping the one or more tracked position, orientation, or movement of UID 126. For example, the console processor can skip the tracking of UID 126, e.g., ignore the UID EM readings while UID 126 is within the range of the distortion. By skipping the tracking, teleoperation of a corresponding actuator 114 may be paused regardless of the spatial state signal received from tracking sensor 304.

As described above, the console processor can use deformation readings from the reference sensor 420 to validate witness EM readings from the witness sensor 410. The validated readings can cause a distortion to be detected. In an embodiment, however, the console processor can ignore the distortion. For example, the console processor may ignore the distortion in response to the deformation being more than a predetermined threshold. More particularly, when the deformation is too large, it can be determined that the distortion reading is faulty, and thus, the console processor may responsively not make adjustments based on the distortion.

Generation of the distortion response signal in response to the detected distortion can include generating a notification of the detected distortion. For example, user console 120 can include an alert mechanism in communication with the processor, and the processor can generate the notification to cause the alert mechanism to indicate one or more of an existence of the distortion, a location of the distortion, or a cause of the distortion. For example, the alert mechanism may be display 128 of user console 120. Display 128 can present the notification or warning to remote operator 107. Alternatively, the alert mechanism may be a speaker used to emit a sound notifying remote operator 107 of the distortion. The alert mechanism may be configured to generate an alert in response to receiving the distortion response signal from the processor.

In an embodiment, the alert generated in response to the distortion response signal is a warning to remote operator 107. The warning may be a visual warning, an audible indicator, a haptic cue, etc. The alert may indicate to remote operator 107 that distortion 401 exists within the EM field. Remote operator 107 may pause movement of UID 126 until the warning ends. The surgical robotic system may automatically pause teleoperation of surgical tool 104 in response to the warning. For example, spatial state signals from UID 126 may be disregarded by console computer system 110, or control signals based on spatial state signals withheld, to prevent movement of surgical tool 104 until the warning ceases.

In an embodiment, the alert provides an indication of the location where the distortion is detected. The processor can determine the location based on the predetermined range 524 of witness sensor 410. For example, when distortion 401 is detected based on a witness EM reading from first witness sensor 502, the processor can notify remote operator 107 that the distortion is likely near the left armrest.

In addition to determining the likely location of the distortion, the processor may monitor a position of UID 126 to determine whether UID 126 is within range 524 of the location. The processor may receive the spatial state signal from tracking sensor 304 to determine a position of UID 126 within EM tracking space 408. When UID 126 is within a range 524 of the mounting location of witness sensor 410 that measures the distortion, the distortion response signal may be generated. The distortion response signal can pause motion of surgical tool 104 based on whether UID 126 is close enough to the distortion. If UID 126 is near witness sensor 410 measuring the distortion, this may indicate an error in the spatial state signal. Accordingly, when the system detects UID 126 is within the range 524 of the location, motion of a corresponding actuator 114 may be paused by the distortion response signal regardless of the spatial state signal received from tracking sensor 304. By contrast, the system may notify remote operator 107 of the presence of the distortion, but may take no action to pause the surgery when UID 126 is not within range of the location. That is, the distortion response signal may not pause teleoperation when UID 126 is outside of range 524 of witness sensor 410 that measures the distortion.

In an embodiment, the distortion response signal can trigger the alert to provide an indication of a cause of the distortion. The alert can provide guidance as to where the distortion is coming from. For example, the alert may be a visual notification that a cause of the distortion is a metal cart passing near the left armrest of user console 120. The processor can determine possible causes of the distortion using reference distortion values, such as quality readings or relative errors. The processor can perform machine learning to identify the likely cause based on the reference distortion values. When the processor identifies a likely cause, the distortion response signal can trigger an alert to suggest to remote operator 107 what may be causing the distortion. Furthermore, the alert can provide guidance or suggestions to reduce the effect. For example, the alert may instruct remote operator 107 to move metal cart 526 outside of range 524 of witness sensor 410 that measures the distortion. Teleoperation of surgical tool 104 may be disengaged while the guidance is provided to remote operator 107. When the cause of the distortion is removed, remote operator 107 may continue teleoperation of surgical tool 104 to perform the surgery.

An EM tracking system is susceptible to magnetic distortion from external objects, such as metal carts, and from sources within the EM tracking space 408. For example, a motor of UID 126, e.g., haptic motor 312, can distort the EM field and degrade the tracking accuracy of the EM tracking system. Actuation of the motor may be the cause of distortion, and thus, the surgical robotic system may include features to minimize the effects of the EM distortion from the known source.

In an embodiment, a structure of UID 126 may reduce the EM distortion caused by actuation of the electronics or the motor within UID 126. For example, the electronics or the motor may be spaced apart from tracking sensor 304 by a distance sufficient to reduce the distortion to a sufficient level. Similarly, the distortion may be reduced to a sufficient level by reducing metallic or non-shielded electronics in UID 126. For example, parts of UID 126 may be fabricated from plastic, silicone, or another non-metallic material. In an embodiment, the electronics or the motor of UID 126 may be shielded to prevent distortion of the EM field. For example, a Faraday cage or another EM shielding structure may be mounted within UID 126 to surround haptic motor 312 and to contain the EM field of haptic motor 312 such that the field does not disrupt operation of tracking sensor 304. The shielding itself may cause distortion, however, a constant consistent distortion may be acceptable for operation of tracking sensor 304. That is, tracking sensor 304 may be monitored to determine relative motion, and not absolute position, and thus, a constant offset of tracking sensor 304 within EM tracking space 408 may not affect performance of surgical tool 104.

Figure 11:
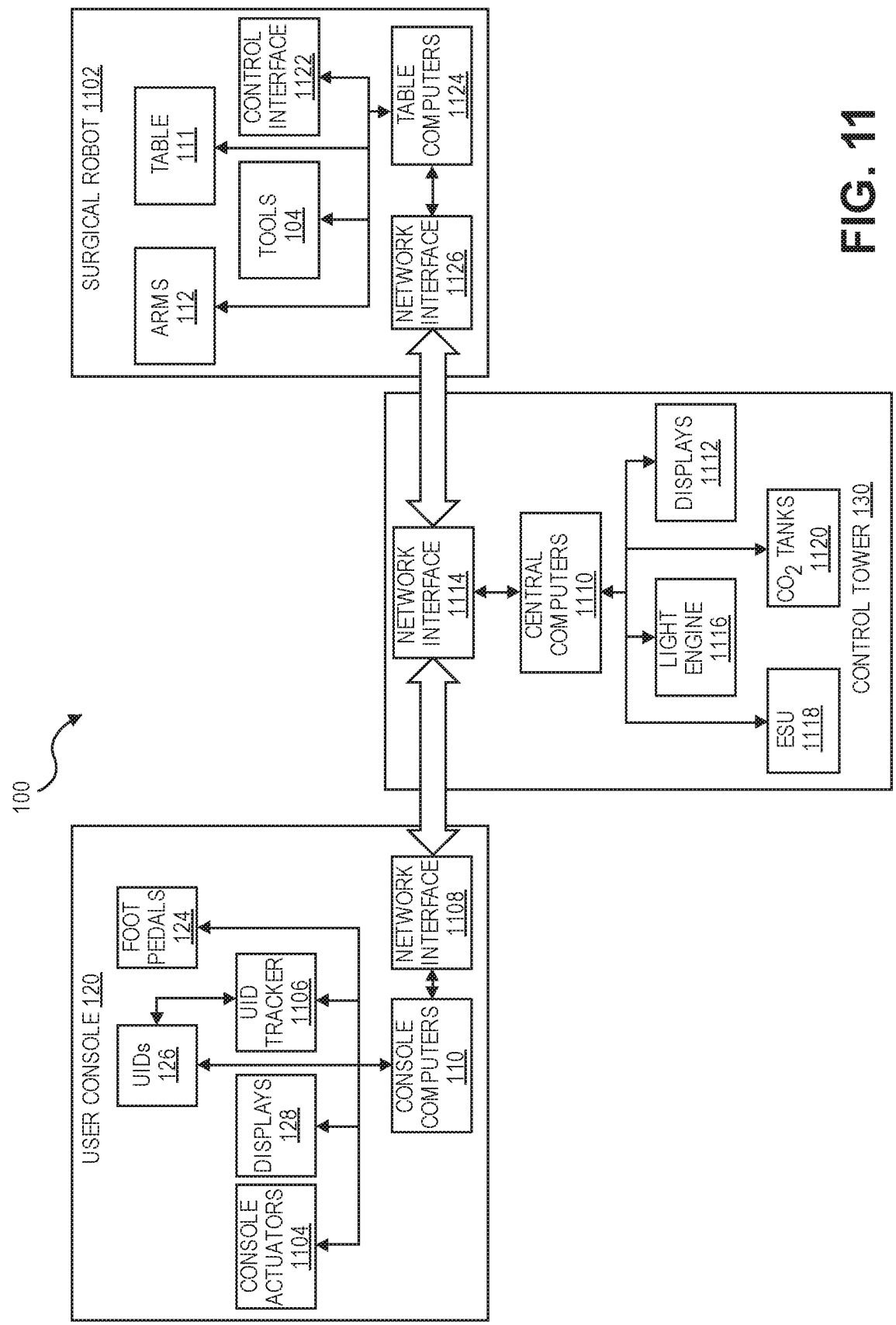
FIG. 11 is a block diagram of a computer portion of a surgical robotic system, in accordance with an embodiment.

In addition to mitigating distortion from the electronics or the motor of UID 126 using structural features, the surgical robotic system may control a manner of sampling data from UID 126 and/or actuating haptic motor 312 of UID 126 to reduce the likelihood that the distortion from haptic motor 312 will affect the spatial state signal. The surgical robotic system can include the processor in communication with tracking sensor 304 and haptic motor 312 of UID 126. For example, the processor may be a console processor (FIG. 11)

contained in console computer system 110. The processor may be configured to sample spatial state signal from tracking sensor 304. The processor may also be configured to control actuation of haptic motor 312, e.g., by generating and applying several actuation pulses to haptic motor 312. The processor can execute instructions contained in a non-transitory computer-readable medium to cause the surgical robotic system to perform the methods described below to reduce the likelihood that sampled data is disrupted by distortions caused by the motor actuation.

Figure 8:
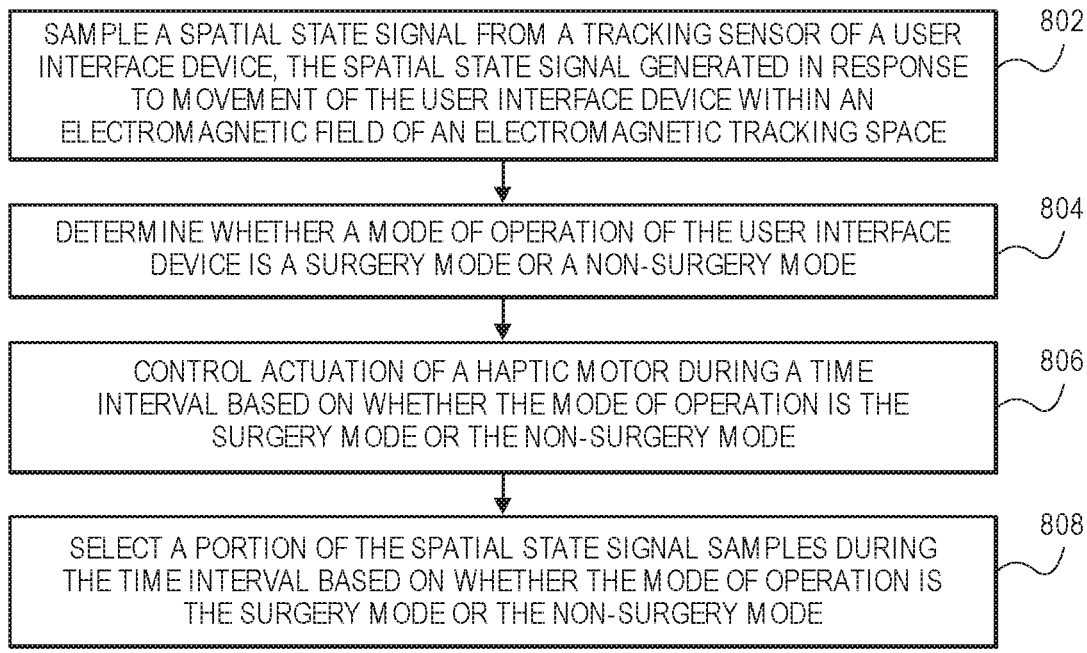
FIG. 8 is a flowchart of a method of monitoring spatial state signals from a user interface device and outputting actuation pulses to a haptic motor of the user interface device, in accordance with an embodiment.

Referring to FIG. 8, a flowchart of a method of monitoring spatial state signals from a user interface device and outputting actuation pulses to a haptic motor of the user interface device is shown in accordance with an embodiment. At operation 802, the processor samples the spatial state signal from tracking sensor 304 of UID 126. Tracking sensor 304 can generate the spatial state signal in response to movement of UID 126 within the EM field of EM tracking space 408, as described above. At operation 804, the processor can determine whether UID 126 is being used in the surgery mode or the non-surgery mode. As described above, UID 126 is used in the surgery mode to control proportional motion of a corresponding actuator 114. UID 126 may be in the non-surgery mode when, for example, remote operator 107 is using UID 126 to control a graphical user interface element on display 128 of user console 120. At operation 806, based on whether UID 126 is being used in the surgery mode or the non-surgery mode, the processor can actuate haptic motor 312 in a particular manner. More particularly, the processor can control actuation of haptic motor 312 during a time interval in a manner to reduce the likelihood that the actuation will disrupt spatial state signal samples. At operation 808, the processor selects a portion of the spatial state signal samples obtained during the time interval based on whether the user interface device is being used in the surgery mode or the non-surgery mode. More particularly, the processor can select the portion of the spatial state signal samples that are unaffected by the actuation of haptic motor 312, or that are affected but will not disrupt control of surgical tool 104.

The method illustrated in FIG. 8 can be adapted to include several operations that respectively reduce the likelihood that sampled data is disrupted by distortions from the motor actuation. In an embodiment, the processor can trigger haptic cues 314 based on whether remote operator 107 is using UID 126 to control coarse movement or fine movement of a controlled element. Coarse movement may correspond to the non-surgery mode and fine movement may correspond to the surgery mode.

The processor may determine that UID 126 is being used in the non-surgery mode based on a velocity of UID 126. The processor can use spatial state signal samples from tracking sensor 304 to determine the velocity. The processor may determine that UID 126 is being used in the non-surgery mode when the velocity is greater than a predetermined velocity threshold. By contrast, the processor may determine that UID 126 is being used in the surgery mode when the velocity is less than the predetermined velocity threshold.

The predetermined velocity threshold may be selected to correspond to a speed at which remote operator 107 moves UID 126 during surgical operations. For example, velocities lower than the predetermined velocity threshold may be consistent with the fine movements made by remote operator 107 when grasping tissue of patient 102. By contrast, velocities higher than the predetermined velocity threshold may be consistent with the coarse movements made by remote operator 107 when using UID 126 to move a cursor on display 128.

The processor may disallow or withhold haptic cues 314 in response to the haptic trigger event when UID 126 is used in the surgery mode. The haptic trigger event can occur during the time interval when the processor gathers spatial state signal samples from tracking sensor 304. Accordingly, the processor may not actuate haptic motor 312 during the time interval when the processor determines that UID 126 is being used in the surgery mode.

The processor may allow or cause haptic cues 314 in response to a haptic trigger event when UID 126 is used in the non-surgery mode. The haptic trigger event can occur during the time interval when the processor gathers spatial state signal samples from tracking sensor 304. Accuracy of spatial state signals may be less important when controlling a cursor element as compared to controlling surgical tool 104, and thus, any error introduced into spatial state signals by haptic motor 312 during the non-surgery mode may be acceptable. Accordingly, the processor may actuate haptic motor 312 during the time interval when the processor determines that UID 126 is being used in the non-surgery mode.

Figure 9:
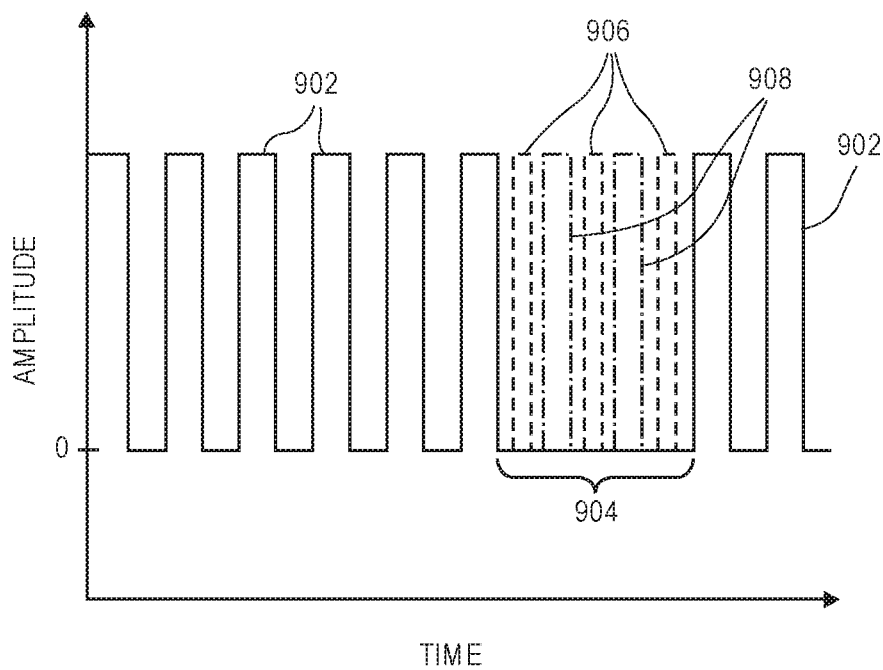
FIG. 9 is a graph of spatial state signal samples received from a user interface device and actuation pulses output to a haptic motor of the user interface device, in accordance with an embodiment.

Referring to FIG. 9, a graph of spatial state signal samples received from a user interface device and actuation pulses output to a haptic motor of the user interface device is shown in accordance with an embodiment. The processor may select spatial state signal samples 902 that are known to be undisrupted by actuation of haptic motor 312. Similarly, the processor may not select spatial state signal samples 902 that may be disrupted by actuation of haptic motor 312. To avoid using spatial state signal samples 902 that are distorted by haptic motor 312, the processor may ignore EM tracker readings while haptic motor 312 is actuated by actuation pulses 906.

As shown in the graph, spatial state signal samples 902 are selected outside of time interval 904 when haptic motor 312 is not being actuated. That is, the selected portion of the spatial state signal from tracking sensor 304 may be none of the spatial state signal samples 902 during the time interval 904. The processor may disregard the spatial state signal samples 902 when UID 126 is being used in the surgery mode. By ignoring one or more of the spatial state signal samples 902 obtained during the time interval 904, surgical tool 104 is controlled by samples obtained when there can be no disruption of the EM field by actuation pulses 906 that are generated and transmitted to haptic motor 312 by the processor.

In an embodiment, the ignored spatial state signal samples 902 from tracking sensor 304 may be supplemented by another sensor of UID 126. For example, the processor may sample a second spatial state signal from IMU 308 of UID 126. Second spatial state signal samples 908 can represent motion of UID 126 irrespective of the EM tracking space 408. For example, the second spatial state signal may include data representing a change in position or orientation of UID 126 without regard to a position of UID 126 within the coordinate space. The processor can select a portion of the second spatial state signal samples 908 during the time interval 904 to control proportional motion of a corresponding actuator 114. The processor may select the portion based on whether UID 126 is being used in the surgery mode or the non-surgery mode. For example, the processor can ignore spatial state signal samples 902 during time interval 904 and select second spatial state signal samples 908 during time interval 904 when UID 126 is being used in the surgery mode.

The processor may employ an algorithm to weight spatial state signal samples 902 and second spatial state signal samples 908 for use in controlling proportional motion of a corresponding actuator 114. Rather than entirely ignoring samples of the spatial state signal from tracking sensor 304, the processor can fuse the data from tracking sensor 304 with the data received from IMU 308 of UID 126. That is, the processor can select samples from both the spatial state signal and the second spatial state signal during the time interval 904. The fusion of data can occur when UID 126 is being used in the surgery mode. Combining tracking data can provide reliable tracking of UID 126 within the EM tracking space 408 when haptic motor 312 is actuated.

The weighting of the data may give more importance to some data over other data. More particularly, the processor may assign respective levels of confidence to the spatial state signal samples 902 and the second spatial state signal samples 908 during the time interval 904. For example, the level of confidence assigned to the second spatial state signal samples 908 may be higher than the level of confidence assigned to the spatial state signal samples 902 when haptic motor 312 is actuated. The level of confidence afforded to second spatial state signal samples 908 can be higher because actuation of haptic motor 312 may affect the sensor readings of IMU 308 less than the sensor readings of tracking sensor 304. The weighting of data from each sensor can allow both spatial state signals to be used, i.e., can allow some use of EM tracking signals during actuation of haptic motor 312.

Figure 10:
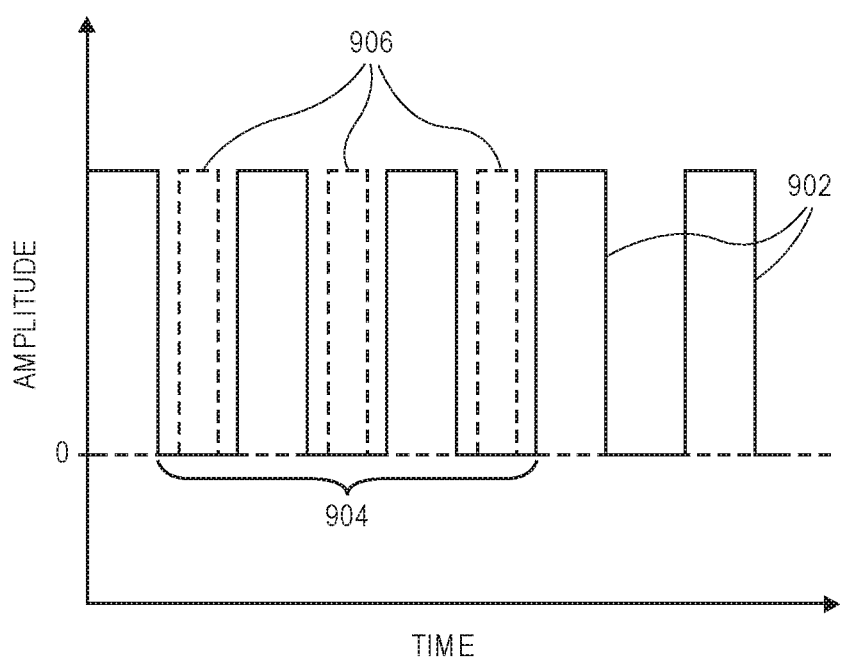
FIG. 10 is a graph of spatial state signal samples received from a user interface device and actuation pulses output to a haptic motor of the user interface device, in accordance with an embodiment.

Referring to FIG. 10, a graph of spatial state signal samples received from a user interface device and actuation pulses output to a haptic motor of the user interface device is shown in accordance with an embodiment. Rather than ignore or devalue the spatial state signal samples 902 received during the time interval 904, the processor may coordinate the timing of sampling and actuation to reduce the likelihood that actuation pulses 906 will disrupt spatial state signal samples 902. In an embodiment, the processor generates and transmits actuation pulses 906 to UID 126 between sampling of spatial state signal samples 902. More particularly, the processor can sample EM tracking data at a same frequency at which haptic motor 312 is actuated. The spatial state signal may be sampled at a sampling frequency, which may be known and constant during operation of the EM tracker. The processor can generate actuation pulses 906 at an actuation frequency. The actuation frequency can be a driving frequency of haptic motor 312. That is, the actuation frequency can be a frequency at which actuation pulses 906 are delivered to haptic motor 312 to generate haptic cues 314. The actuation frequency can be equal to the sampling frequency. The actuation pulses 906 can be interjected between samples gathered from tracking sensor 304. For example, the processor may apply a phase shift between the actuation signal and the sample time. Each actuation pulse 906 may begin after a preceding spatial state signal sample 902, and may end before a next spatial state signal sample 902. Thus, the actuation pulses 906 can be interlaced with the spatial state signal samples 902.

Referring to FIG. 11, a block diagram of a computer portion of a surgical robotic system is shown in accordance with an embodiment. The exemplary surgical robotic system 100 may include a user console 120, a surgical robot 1102, and a control tower 130. The surgical robotic system 100 may include other additional hardware components; thus, the diagram is provided by way of example and not limitation to the system architecture.

As described above, the user console 120 comprises console computers 110 and one or more UIDs 126. User console 120 can include console actuators 1104, displays 128, a UID tracker 1106, foot pedals 124, and a network interface 1108. A user or surgeon sitting at the user console 120 can adjust ergonomic settings of the user console 120 manually, or the settings can be automatically adjusted according to the user profile or preference. The manual and automatic adjustments may be achieved through driving the console actuators 1104 based on user input or stored configurations by the console computers 110. The user may perform robot-assisted surgeries by controlling the surgical robot 1102 using two master UIDs 126 and foot pedals 124. Positions and orientations of the UIDs 126 are continuously tracked by the UID tracker 1106, and status changes are recorded by the console computers 110 as user input and dispatched to the control tower 130 via the network interface 1108. Real-time surgical video of patient anatomy, instrumentation, and relevant software apps can be presented to the user on the high resolution 3-D displays 128 including open or immersive displays.

Unlike other existing surgical robotic systems, the user console 120 disclosed herein may be communicatively coupled to the control tower 130 over a single fiber optic cable. The user console also provides additional features for improved ergonomics. For example, both an open and immersive display are offered compared to only an immersive display. Furthermore, a highly-adjustable adjustable seat for surgeons and master UIDs tracked through EM or optical trackers are included at the user console 120 for improved ergonomics. To improve safety, eye tracking, head tracking, and/or seat swivel tracking can be implemented to prevent accidental tool motion, for example, by pausing or locking teleoperation when the user's gaze is not engaged in the surgical site on the open display for over a predetermined period of time.

The control tower 130 can be a mobile point-of-care cart housing touchscreen displays, computers that control the surgeon's robotically-assisted manipulation of instruments, safety systems, graphical user interface (GUI), light source, and video and graphics computers. As shown in FIG. 11, the control tower 130 may comprise central computers 1110 including at least a visualization computer, a control computer, and an auxiliary computer, various displays 1112 including a team display and a nurse display, and a network interface 1114 coupling the control tower 130 to both the user console 120 and the surgical robot 1102. The control tower 130 may also house third-party devices, such as an advanced light engine 1116, an electrosurgical generator unit (ESU) 1118, and insufflator and CO2 tanks 1120. The control tower 130 may offer additional features for user convenience, such as the nurse display touchscreen, soft power and E-hold buttons, user-facing USB for video and still images, and electronic caster control interface. The auxiliary computer may also run a real-time Linux, providing logging/ monitoring and interacting with cloud-based web services.

The surgical robot 1102 comprises an articulated operating table 111 with a plurality of integrated arms 112 that can be positioned over the target patient anatomy. A suite of compatible tools 104 can be attached to or detached from the distal ends of the arms 112, enabling the surgeon to perform various surgical procedures. The surgical robot 1102 may also comprise control interface 1122 for manual control of the arms 112, table 111, and tools 104. The control interface can include items such as, but not limited to, remote controls, buttons, panels, and touchscreens. Other accessories such as trocars (sleeves, seal cartridge, and obturators) and drapes may also be needed to perform procedures with the system. In some variations the plurality of arms 112 include forearms mounted on both sides of the operating table 111, with two arms on each side. For certain surgical procedures, an arm mounted on one side of the table can be positioned on the other side of the table by stretching out and crossing over under the table and arms mounted on the other side, resulting in a total of three arms positioned on the same side of the table 111. The surgical tool can also comprise table computers 1124 and a network interface 1126, which can place the surgical robot 1102 in communication with the control tower 130.

The following statements of invention are supported by the above description. In an embodiment, a user console includes a user interface device incorporating a tracking sensor and a haptic motor. The tracking sensor generates a spatial state signal in response to movement of the user interface device within an EM field of an EM tracking space. The haptic motor is capable of generating a haptic cue when actuated. The user interface device is used in a surgery mode and a non-surgery mode, and the spatial state signal is used in the surgery mode to control proportional motion of a corresponding actuator. A processor is configured to sample the spatial state signal from the tracking sensor. The processor is configured to determine whether the user interface device is being used in the surgery mode or the non-surgery mode. The processor is configured to control actuation of the haptic motor during a time interval based on whether the user interface device is being used in the surgery mode or the non-surgery mode. The processor is configured to select a portion of the spatial state signal samples during the time interval based on whether the user interface device is being used in the surgery mode or the non-surgery mode. In one embodiment, the processor is configured to determine a velocity of the user interface device based on the spatial state signal samples. The processor is configured to determine that the user interface device is being used in the non-surgery mode when the velocity is greater than a predetermined velocity threshold. The processor is configured to determine that the user interface device is being used in the surgery mode when the velocity is less than the predetermined velocity threshold. In one embodiment, the processor is configured to not actuate the haptic motor in response to a haptic trigger event during the time interval when the processor determines that the user interface device is being used in the surgery mode. The processor is configured to actuate the haptic motor in response to the haptic trigger event during the time interval when the processor determines that the user interface device is being used in the non-surgery mode. In one embodiment, the selected portion is none of the spatial state signal samples during the time interval when the processor determines that the user interface device is being used in the surgery mode. In one embodiment, the user interface device further includes an inertial measurement unit to generate a second spatial state signal in response to movement of the user interface device. The processor is configured to sample the second spatial state signal from the inertial measurement unit. The processor is configured to select a portion of the second spatial state signal samples during the time interval based on whether the user interface device is being used in the surgery mode or the non-surgery mode. In one embodiment, the processor selects samples from both the second spatial state signal and the spatial state signal during the time interval when the user interface device is being used in the surgery mode. In one embodiment, the processor is configured to assign respective levels of confidence to the spatial state signal samples and the second spatial state signal samples. The level of confidence assigned to the second spatial state signal samples is higher than the level of confidence assigned to the spatial state signal samples during the time interval. In one embodiment, the processor controls actuation of the haptic motor by generating a plurality of actuation pulses. In one embodiment, the processor is configured to generate the plurality of actuation pulses between sampling spatial state signal samples. In one embodiment, the processor is configured to generate the plurality of actuation pulses at an actuation frequency. The processor is configured to sample the spatial state signal at a sampling frequency equal to the actuation frequency. The plurality of actuation pulses are interlaced with the spatial state signal samples.

In an embodiment, a method includes sampling, by a processor, a spatial state signal from a tracking sensor of a user interface device. The tracking sensor generates the spatial state signal in response to movement of the user interface device within an EM field of an EM tracking space. The method includes determining, by the processor, whether the user interface device is being used in a surgery mode or a non-surgery mode. The user interface device is used in the surgery mode to control proportional motion of a corresponding actuator. The method includes controlling, by the processor, actuation of a haptic motor within the user interface device during a time interval based on whether the user interface device is being used in the surgery mode or the non-surgery mode. The method includes selecting, by the processor, a portion of the spatial state signal samples during the time interval based on whether the user interface device is being used in the surgery mode or the non-surgery mode.

In an embodiment, a non-transitory computer-readable medium including instructions, which when executed by a processor of a user console, cause the user console to perform a method including sampling, by a processor, a spatial state signal from a tracking sensor of a user interface device. The tracking sensor generates the spatial state signal in response to movement of the user interface device within an EM field of an EM tracking space. The method includes determining, by the processor, whether the user interface device is being used in a surgery mode or a non-surgery mode. The user interface device is used in the surgery mode to control proportional motion of a corresponding actuator. The method includes controlling, by the processor, actuation of a haptic motor within the user interface device during a time interval based on whether the user interface device is being used in the surgery mode or the non-surgery mode. The method includes selecting, by the processor, a portion of the spatial state signal samples during the time interval based on whether the user interface device is being used in the surgery mode or the non-surgery mode.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A user console for a surgical robot, comprising:
an electromagnetic (EM) generator mounted on the user console and configured to generate an EM field;

an ungrounded user interface device (UID) having one or more UID EM sensors configured to generate UID EM readings of the EM field;
a stationary witness sensor mounted on the user console and configured to generate witness EM readings of the EM field;
a reference sensor mounted on the user console and configured to generate deformation readings in response to a deformation or a movement of the user console; and
a processor communicatively coupled to the UID, the witness sensor, and the reference sensor, wherein the processor is configured to:
 track one or more of a position, an orientation, or a movement of the UID based on the UID EM readings,
 detect a distortion in the EM field based on the witness EM readings and the deformation readings, and
 adjust the one or more tracked position, orientation, or movement of the UID based on the detected distortion.

2. The user console of claim 1, wherein the reference sensor is mounted on the user console adjacent to the witness sensor.

3. The user console of claim 1, wherein the processor detects the distortion when the witness EM readings reflect the distortion in the EM field and the deformation readings reflect that the deformation is less than a deformation threshold.

4. The user console of claim 1, wherein the witness sensor is an EM sensor, and wherein the reference sensor is a non-EM sensor.

5. The user console of claim 1 further comprising a second witness sensor mounted on the user console and configured to generate second witness EM readings of the EM field, wherein the processor is communicatively coupled to the second witness sensor, and wherein the processor is configured to detect distortion in the EM field when the witness EM readings and the second witness EM readings reflect a distance change between the witness sensor and the second witness sensor.

6. The user console of claim 1, wherein the processor is configured to generate a notification in response to detecting the distortion.

7. The user console of claim 6, wherein the notification indicates one or more of an existence of the distortion, a location of the distortion, or a cause of the distortion.

8. The user console of claim 1, wherein the processor is configured to adjust the one or more tracked position, orientation, or movement of the UID based on whether the UID is within a range of the detected distortion.

9. The user console of claim 8, wherein the UID EM readings from the UID are used to control proportional motion of a corresponding actuator, and wherein the processor pauses motion of the corresponding actuator when the UID is within the range of the detected distortion.

10. A surgical robotic system, comprising:
a user console including an electromagnetic (EM) generator, a stationary witness sensor, and a reference sensor mounted on the user console, wherein the EM generator is configured to generate an EM field, wherein the witness sensor is configured to generate witness EM readings of the EM field, and wherein the reference sensor is configured to generate deformation readings in response to a deformation or a movement of the user console;
a user interface device (UID) configured to generate UID EM readings of the EM field; and
a processor configured to:
 track one or more of a position, an orientation, or a movement of the UID based on the UID EM readings,
 detect a distortion in the EM field based on the witness EM readings and the deformation readings, and
 generate a notification of the detected distortion.

11. The surgical robotic system of claim 10, wherein the reference sensor is mounted on the user console adjacent to the witness sensor.

12. The surgical robotic system of claim 10, wherein the UID includes a UID EM sensor to generate the UID EM readings.

13. The surgical robotic system of claim 10, wherein the processor detects the distortion when the witness EM readings reflect the distortion in the EM field and the deformation readings reflect that the deformation is less than a deformation threshold.

14. The surgical robotic system of claim 10, wherein the notification indicates one or more of an existence of the distortion of the EM field, a location of the distortion, or a cause of the distortion.

15. The surgical robotic system of claim 10, wherein the processor is configured to adjust the one or more tracked position, orientation, or movement of the UID based on whether the UID is within a range of the detected distortion.

16. A method of detecting distortions in an electromagnetic (EM) tracking field in a surgical robotic system, the method comprising:
receiving, from a user interface device (UID) of a user console of the surgical robotic system, UID EM readings of the EM tracking field;
receiving, from a stationary witness sensor mounted on the user console, witness EM readings of the EM tracking field;
receiving, from a reference sensor mounted on the user console, deformation readings in response to a deformation or a movement of the user console; and
detecting, by a processor, distortion of the EM field based on the witness EM readings and the deformation readings.

17. The method of claim 16 further comprising:
tracking, by the processor, one or more of a position, an orientation, or a movement of the UID based on the UID EM readings; and
adjusting, in response to detecting the distortion, the tracking of the one or more of the position, the orientation, or the movement of the UID.

18. The method of claim 17, wherein adjusting the tracking of the one or more of the position, the orientation, or the movement of the UID is in response the UID being within a range of the detected distortion and the deformation being less than a deformation threshold.

19. The method of claim 17, wherein adjusting the tracking of the one or more of the position, the orientation, or the movement of the UID includes skipping the tracking of the one or more of position, orientation, or movement of the UID when the UID is within a range of the distortion.

20. The method of claim 16 further comprising ignoring, by the processor, the distortion.

21. The method of claim 20, wherein ignoring, by the processor, the distortion is in response to the deformation being more than a deformation threshold.

* * * * *